United States Patent
Ghodrati (10) Patent No.: US 8,862,214 B2
(45) Date of Patent: Oct. 14, 2014

(54) CARDIAC CONDITION DETECTION SYSTEM

(75) Inventor: Alireza Ghodrati, North Andover, MA (US)

(73) Assignee: Draeger Medical Systems, Inc., Andover, MA (US)

(*) Notice: Subject to any disclaimer, the term of this patent is extended or adjusted under 35 U.S.C. 154(b) by 647 days.

(21) Appl. No.: 12/935,060

(22) PCT Filed: Apr. 2, 2009

(86) PCT No.: PCT/US2009/039298
§ 371 (c)(1),
(2), (4) Date: Sep. 28, 2010

(87) PCT Pub. No.: WO2009/124187
PCT Pub. Date: Oct. 8, 2009

(65) Prior Publication Data
US 2011/0021935 A1  Jan. 27, 2011

Related U.S. Application Data

(60) Provisional application No. 61/042,331, filed on Apr. 4, 2008.

(51) Int. Cl.
| A61B 5/04 | (2006.01) |
| A61N 1/00 | (2006.01) |
| A61B 5/024 | (2006.01) |
| A61N 1/362 | (2006.01) |
| A61B 5/0464 | (2006.01) |
| A61N 1/39 | (2006.01) |

(52) U.S. Cl.
CPC .......... *A61B 5/024* (2013.01); *A61N 1/362* (2013.01); *A61B 5/02405* (2013.01); *A61B 5/0464* (2013.01); *A61N 1/39* (2013.01)
USPC ............................................ 600/519; 607/14

(58) Field of Classification Search
USPC ........................................ 600/519; 607/14, 4
See application file for complete search history.

(56) References Cited

U.S. PATENT DOCUMENTS

| 3,633,569 A | 1/1972 | Brayshaw et al. |
| 5,411,031 A | 5/1995 | Yomtov |

(Continued)

FOREIGN PATENT DOCUMENTS

| WO | WO/02/069178 | 9/2002 |
| WO | WO/03/077755 | 9/2003 |
| WO | WO/03/105020 | 12/2003 |

OTHER PUBLICATIONS

"Time Domain Measurement of Heart Rate Variability"; Marek Malik; Cardiac Electrophysiology Review; pp. 329-334; 1997.

(Continued)

*Primary Examiner* — Catherine Voorhees
(74) *Attorney, Agent, or Firm* — Jack Schwartz and Associates, PLLC (57) ABSTRACT

A system is provided which processes cardiac condition data representative of heart electrical signals to identify a cardiac condition. An acquisition processor is conditioned for acquiring data representing a sequence of successive pulses of a type of electrical heart waveform of a patient. A computation processor is electrically coupled to the acquisition processor and is conditioned for calculating a pulse interval irregularity measure based on a sum of time interval differences occurring between pairs of successive pulses of the sequence of successive pulses and excluding time interval differences exceeding a predetermined maximum threshold from the sum. The computation processor is further conditioned to compare a calculated pulse interval irregularity measure with a predetermined irregularity measure threshold. An output processor is electrically coupled to the computation processor and conditioned for generating data representing an alarm message in response to the calculated pulse interval irregularity measure exceeding the predetermined threshold.

20 Claims, 5 Drawing Sheets

(56) References Cited

U.S. PATENT DOCUMENTS

| | | | |
|---|---|---|---|
| 5,480,413 A * | 1/1996 | Greenhut et al. | 607/14 |
| 5,591,215 A | 1/1997 | Greenhut et al. | |
| 6,496,731 B1 | 12/2002 | Lovett | |
| 6,597,943 B2 | 7/2003 | Taha et al. | |
| 7,020,514 B1 | 3/2006 | Wiesel | |
| 7,120,485 B2 | 10/2006 | Glass et al. | |
| 7,596,405 B2 | 9/2009 | Kurzweil et al. | |
| 2006/0084883 A1 | 4/2006 | Linker | |
| 2006/0276716 A1 | 12/2006 | Healey et al. | |
| 2007/0073177 A1 | 3/2007 | Kontothanassis et al. | |

OTHER PUBLICATIONS

"A Comparative Study of a Hidden Markov Model Detector for Atrial Fibrillation"; Young et al.; 1999 IEEE; pp. 468-476.

"A Method for Detection of Atrial Fibrillation using RR Intervals"; K Tateno Et Al.; Computers in Cardiology 2000; vol. 27; pp. 391-394.

"Atrial Fibrillation Dection Algorithms for Very Long Term ECG Monitoring"; E. Pertucci Et Al..; Computers for Cardiology; 2005 vol. 32; pp. 623-626.

"Review of Methods to Predict and Detect Atrial Fibrillation in Post-Cardiac Surgery Patients"; Reddy Et Al.; Journal of Electrocardiology vol. 32 Supplement 1999; pp. 23-28.

"Robust Detection of Atrial Fibrillation for a Long Term Telemonitoring System"; BT Logan Et Al.; IEEE Computers in Cardiology; pp. 25-28 Sep. 2005.

"The Principles of Sotware QRS Detection"; Kohler Et Al.; Engineering and Biology; Jan./Feb. 2002; pp. 42-57.

* cited by examiner

|RR2-RR1|=0
|RR3-RR2|=24ms
|RR4-RR3|=4ms
|RR5-RR4|=0
|RR6-RR5|=24ms
|RR7-RR6|=244ms
|*RR8-RR7|=352ms (This will be excluded since it is higher than the threshold)*
|RR9-RR8|=152ms
|RR10-RR9|=36ms

CARDIAC CONDITION DETECTION SYSTEM

CROSS-REFERENCE TO RELATED APPLICATIONS

This Application claims priority from U.S. Provisional Patent Application Ser. No. 61/042,331 filed on Apr. 4, 2008 by Alireza Ghodrati.

FIELD OF THE INVENTION

This invention concerns a system and method for analyzing cardiac electrophysiological signals for use in making decisions affecting cardiac medical treatment.

BACKGROUND OF THE INVENTION

Atrial Fibrillation (AFIB) is a common sustained rhythm disturbance. Its prevalence is increasing along with age. In prospective studies, the incidence of AFIB increased from less than 0.1% per year in people under 40 to greater than 1.5% per year in women over 80 and greater than 2% in men over 80 years of age. The rate of ischemic stroke among patients with AFIB is between 2 to 7 times that of people without AFIB.

AFIB is a common arrhythmia in patients who have undergone cardiac surgery. It is estimated that almost 1 in 5 patients admitted to intensive care unit will develop atrial fibrillation. Experts from American Heart Association's Council recommend continuous monitoring for patients at high risk for developing postoperative atrial fibrillation until hospital discharge. Therefore there is a need for a reliable AFIB detection system in ECG monitoring devices.

Atrial fibrillation (AFIB) is a supraventricular tachyarrhythmia characterized by uncoordinated atrial activation with consequent deterioration of atrial mechanical function. On the surface electrocardiogram, AFIB is described by the replacement of consistent P waves by rapid oscillations or fibrillatory waves that vary in size, shape, and timing, resulting in an irregular, frequently rapid ventricular response. The irregularity of the heart rate and absence of the normal P wave are important features in detecting AFIB from the ECG signals. However heart rate irregularity exists in many other rhythms such as AV blocks or due to atrial premature beats (APB).

Known methods of AFIB detection are typically based only on RR interval irregularity involving determining an irregularity measure by simple methods like variance of selected RR intervals or more sophisticated methods such as a Markov model, Neural Network and Hidden Markov Model. Simple measures typically attempt to capture and quantify the randomness of RR intervals while modeling approaches try to construct a model for RR irregularity. Given the chaotic nature of AFIB it is unlikely to model the exact behavior of RR irregularity during AFIB. However the models are usually helpful in distinguishing RR irregularity of AFIB from those caused by other cardiac arrhythmias which is the biggest challenge of AFIB detection. Known systems exhibit excessive false positive detection of AFIB e.g. caused by analysis of non-AFIB rhythms. Known systems also exhibit low sensitivity in detection of short episodes of AFIB. A system according to invention principles addresses deficiencies of known systems to improve cardiac condition detection.

SUMMARY OF THE INVENTION

A system is provided which processes cardiac condition data representative of heart electrical signals to identify a cardiac condition. An acquisition processor is conditioned for acquiring data representing a sequence of successive pulses of a type of electrical heart waveform of a patient. A computation processor is electrically coupled to the acquisition processor and is conditioned for calculating a pulse interval irregularity measure based on a sum of time interval differences occurring between pairs of successive pulses of the sequence of successive pulses and excluding time interval differences exceeding a predetermined maximum threshold from the sum. The computation processor is further conditioned to compare a calculated pulse interval irregularity measure with a predetermined irregularity measure threshold. An output processor is electrically coupled to the computation processor and conditioned for generating data representing an alarm message in response to the calculated pulse interval irregularity measure exceeding the predetermined threshold.

DETAILED DESCRIPTION

A cardiac condition detection system 10 (FIG. 1) according to invention principles employs one or multiple different (alternatively or concurrently usable) RR irregularity measures suitable for AFIB detection in ECG monitors. A first measure is based on absolute deviation and a second is based on the difference between successive RR intervals. The system 10 advantageously employs constraints for RR interval data used by an irregularity measure generator to exclude RR, irregularities caused by measurement noise or other cardiac arrhythmias. In one embodiment, one or more parameters of the system, e.g., a threshold measure against which data acquired from the patient is compared, an irregularity measure threshold, or a maximum time interval threshold, are derived by a training process implemented prior to system operation using at least one database including a plurality of sets of data representing heart electrical signals. In a further embodiment, system 10 utilizes at least one database that includes a plurality of sets of data representing heart electrical signals. Each set of data in the at least one data base includes arrhythmia data which advantageously enables the system to compare an irregularity value calculated according to the system implemented algorithm with stored patient data that is indicative of AFIB arrhythmias. Exemplary databases used in developing and training the system, will be discussed hereinafter with respect to FIGS. 6-8.

The system 10 generates different irregularity values enabling more precise AFIB detection. The irregularity values employ RR interval representative data. System 10 employs a classification of beats that excludes known cardiac signal deviations that may incorrectly identify a currently monitored set of cardiac heart signal data as AFIB. For example, RR, intervals bounded by Ventricular Premature Beats (VPB) from either side may lead to an alert being generated indicating that a patient is in AFIB. By automatically detecting and excluding the VPB data value from being used by system 10, a healthcare professional is prevented from receiving a false positive indicator of AFIB. Additionally, system 10 employs threshold value constraints on RR intervals for each method to improve their performance by improving the ability to eliminate false detections of AFIBs. The calculated irregularity values are compared against a threshold value and AFIB is determined in response to a generated irregularity measure if the corresponding irregularity measure is greater than a predetermined threshold. The irregularity measures and associated interval constraints are described as follows.

A first measure used in determining if an series of successive electrical pulse signals representing a patient heartbeat (ECG frame) is the Normalized Absolute Deviation (NADev) of RR intervals. The NADev of a frame of ECG signals containing M intervals is, $$NADev = \sum_{i=1}^{M} \frac{|RR_i - \overline{RR}|}{M * \overline{RR}}$$

where $\overline{RR}$ is the mean of RR intervals and $||$ represents the absolute value. NADev is used in preference to a Normalized Standard Deviation (NSDev) because it is computationally less complex but also has more emphasis on global RR irregularity. Observations indicate AFIB often involves relatively small RR irregularities in most of the beats while measurement noise and other rhythms usually cause large irregularities in a small number of beats. Therefore NADev results in a better detection performance than NSDev against noise and other rhythms involving RR irregularities. The system advantageously employs a constraint on RR intervals that are used to generate an irregularity measure in order to exclude very large and very small RR intervals in a frame. By actively excluding these large and small RR intervals, system 10 is able to decrease false AFIB detection caused by non-AFIB rhythms. Specifically, an interval $RR_i$ is used in the calculation if $$\alpha\overline{RR} < RR_i < \beta\overline{RR}$$

where $\alpha < 1$ and $\beta > 1$.

A second measure used in determining if a series of successive electrical pulse signals representing a patient heartbeat (ECG frame) is the Normalized Absolute Difference (NADiff) of RR intervals. The NADiff of RR intervals of a frame of ECG signal containing M intervals is, $$NADiff = \frac{\sum_{i=1}^{M-1} |RR_{i+1} - RR_i|}{(M-1) \times \overline{RR}}$$

System 10 employs an algorithm that uses the absolute value rather than the square of the RR intervals to emphasize global irregularity which results in improved detection of AFIB. Interval differences larger than a fixed threshold ($|RR_i - RR_{i-1}| > \gamma$) are also advantageously excluded to decrease the effect of measurement noise and non-AFIB rhythms. The NADev measure and NADiff measure may be used alone or in combination with one another in order to minimize false positive identification of patient AFIB. Alone or together, these measures provide a basis for an improve AFIB detection algorithm implemented by system 10.

Figure 1:
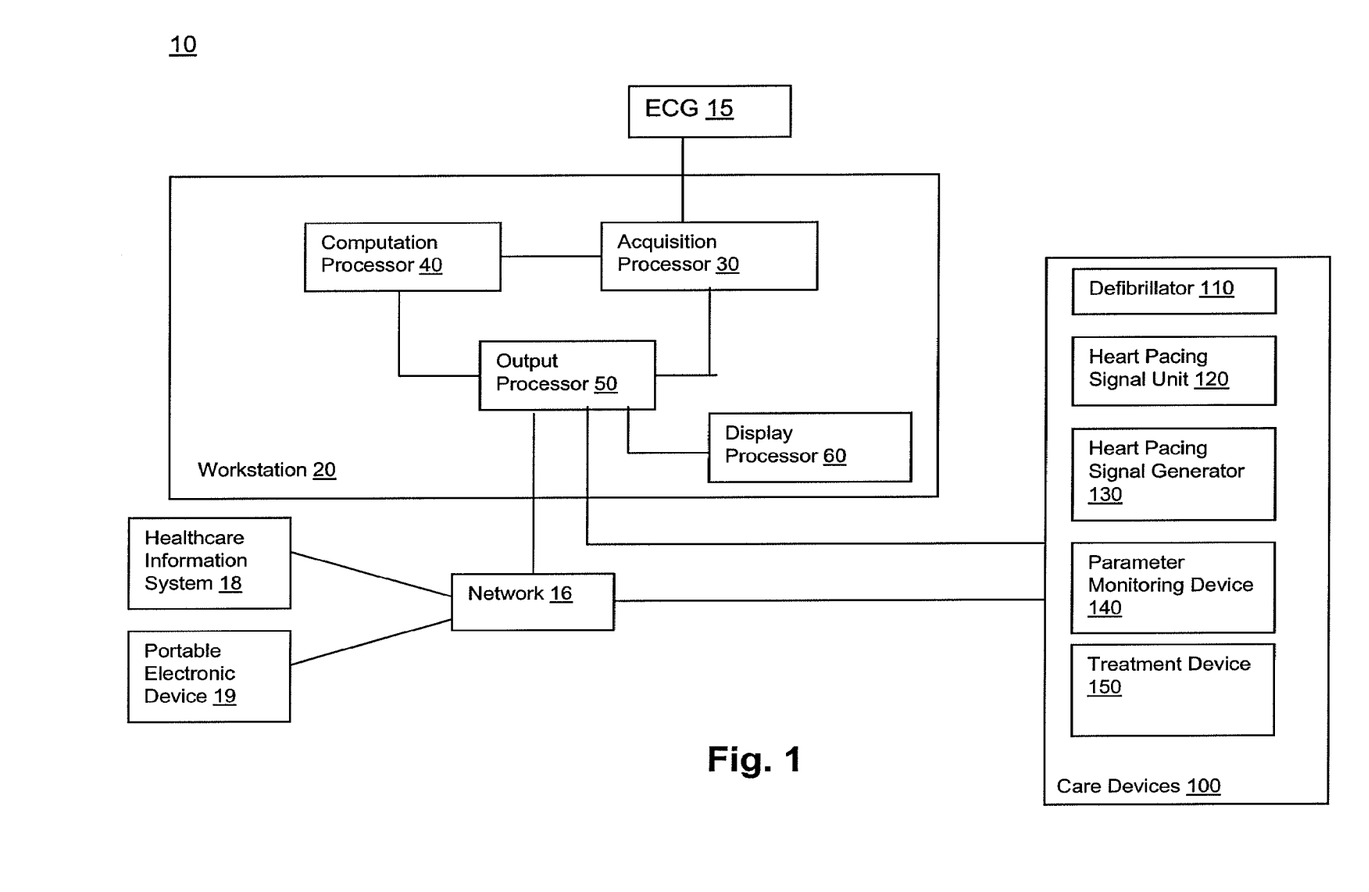
FIG. 1 shows a cardiac condition detection system according to invention principles.

FIG. 1 is a block diagram of the cardiac condition detection system 10. System 10 includes a plurality of specifically purposed processors that are electrically connected to one another via electronic circuitry and conditioned to implement and/or operate according to an algorithm. The processors may be responsive to an executable application. A processor is a hardware device that operates in accordance with a set of instructions encoded thereon. A processor acts upon information by manipulating, analyzing, modifying, converting or transmitting information for use by an executable procedure or an information device, and/or by routing the information to an output device. A processor is a physical computing device and may use or comprise the capabilities of a controller or microprocessor, for example. A processor may be electrically coupled to any other processor enabling interaction and/or communication therebetween. An executable application, as used herein, comprises code or machine readable instructions for conditioning a processor to implement predetermined functions, such as those of an operating system, a context acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A display processor or generator is a known element comprising electronic circuitry responsive to a set of executable applications and/or procedures or a combination of both for generating display images or portions thereof.

A user interface (UI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application manipulates the UI display images in response to the signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without direct user initiation of the activity.

System 10 includes an ECG monitor 15 that is coupled to a patient for sensing electrical heart beat signals from the patient. ECG monitor 15 is connected to a workstation 20 that includes electronic circuitry that is conditioned to operate according to a predetermined algorithm for calculating and determining a value representing an irregularity measure from a series of successive electrical heartbeat signals sensed by ECG monitor 15. Workstation 20 may be any of a bedside patient monitoring device, a centralized monitoring station, for example a nursing station or a combination of both. Additionally, the circuitry described hereinbelow and included in workstation 20 may be incorporated into a device comprising the ECG monitor 15.

Workstation 20 includes an acquisition processor 30 that is conditioned to communicate with ECG monitor 15 and acquire data representing the sensed electrical heartbeat signals from the ECG monitor 15 for a particular patient. Acquisition processor 30 operates according to an algorithm to acquire data representing individual heartbeat signals to generate a sequence of successive pulses of an electrical heartbeat waveform. Successively acquired data representing an individual heartbeat signal is combined to generate data representing an ECG frame. The data representing a sequence of successive pulses of a type of electrical heart waveform of a patient acquired by the acquisition processor includes R-wave pulses and each pulse of successive pulses corresponds to a normal heart beat.

Workstation 20 further includes computation processor 40 electrically coupled to acquisition processor 30. Computation processor 40 is conditioned to calculate pulse interval irregularity measures associated with an ECG frame derived by acquisition processor 30 from ECG monitor 15. The computation processor calculates a pulse interval irregularity measure based on a sum of time interval differences occurring between pairs of successive pulses of the sequence of successive pulses. Time interval differences exceeding a predetermined maximum threshold (at least 290 ms) are excluded from the sum and a calculated pulse interval irregularity measure is compared with a predetermined irregularity measure threshold. An individual time interval difference comprises a difference between a first time interval occurring between a first pair of pulses and a second time interval occurring between a subsequent second pair of pulses, said first and second pair of pulses sharing a common pulse. The predetermined maximum threshold employed by system 10 is adaptively varied in response to at least one of, (a) mean pulse time interval size, (b) number of pairs of consecutive normal heart beats between a sequence of successive pulses and (c) a previously calculated irregularity measure value. A predetermined irregularity measure threshold employed by system 10 is adaptively varied in response to at least one of, (a) mean pulse time interval size, (b) number of pairs of consecutive normal heart beats between a sequence of successive pulses and (c) a previously calculated irregularity measure value.

The computation processor inhibits calculation if the number of pairs of consecutive normal heart beats in a first predetermined number of successive heart beats is less than a second predetermined number, for example, the first predetermined number may be 5 and the second predetermined number is at least 30. The computation processor may also calculate the pulse interval irregularity measure based on a sum of the absolute value of the time interval differences. The computation processor may also calculates the pulse interval irregularity measure by dividing the sum of the absolute value of the time interval differences by a mean of the pulse intervals. The computation processor may also calculate the pulse interval irregularity measure by dividing the sum of the absolute value of the time interval differences by the mean of the pulse intervals multiplied by the number of intervals involved. The computation processor may also calculate the irregularity measure δ as:

$$\delta = \sum_{i=2}^{M} \frac{|RR_i - RR_{i-1}|}{(M-1)*\overline{RR}}$$

where RR represent the interval between two consecutive R waves, $\overline{RR}$ is the mean value of the selected RR intervals and $|RR_i - RR_{i-1}|$ represents the absolute value thereof.

Output processor 50 is electrically connected to each of acquisition processor 30 and computation processor 40. Output processor 50 is conditioned to generate data representing an alert message in response to the calculated pulse interval irregularity measure exceeding a predetermined threshold. Output processor 50 is further conditioned to generate message data including data representing (a) the sequence of successive pulses of an electrical heart waveform of the patient acquired by acquisition processor 30, (b) a pulse interval irregularity measure calculated by the computation processor 40, (c) a particular irregularity measure threshold used in the comparison including source information representing the repository from which the threshold value is derived, (d) a calculated individual time interval difference value, and (e) data representing a destination address to which an alert message is communicated. Message data also includes patient identifier information including data representing at least one of (a) patient name, (b) patient ID number and (c) patient location information. Message data generated by output processor 50 may be communicated to a destination system, for example a healthcare information system 18 and/or a portable electronic device (e.g. PDA, cellphone, mobile computing device, etc). Message data communicated to destination system is used for providing real-time monitoring of the particular patient by a healthcare professional. Message data received by the destination system may be parsed and used to automatically update a patient healthcare record. For example, upon receiving message data indicating that an AFIB has occurred in view of the irregularity value calculated by computation processor 40, healthcare information system 18 parses message data and uses patient identification information to update a patient healthcare record corresponding thereto with clinical data (i.e. irregularity measurements).

Output processor 50 is also conditioned to generate control data responsive to the alert message for controlling at least one patient care device 100. Patient care devices include, for example, defibrillator 110, heart pacing signal unit 120, heart pacing signal generator 130, patient parameter monitoring device 140 and patient treatment device 150. In response to the alert message, a user is notified to initiate defibrillation in response to the alert message. Alternatively, in response to the alert message, control data is automatically generated and communicated to defibrillator 110 and includes instructions for automatically initiating defibrillation in response to the alert message. The instructions in defibrillator control data includes voltage data and duration data identifying a duration of defibrillation. Control data generated by output processor 50 in response to alert message may also be communicated to at least one of heart pacing signal generator 130 and heart pacing signal unit 120 for automatically initiating generation of a heart pacing signal in response to the alert message or for automatically providing a heart pacing signal to a patient heart in response to the alert message. Control data generated by output processor 50 in response to the alert message may also be communicated to patient parameter monitoring device 140 for automatically changing monitoring device operational settings in response to the alert message, for example the patient parameter monitoring device may be an ECG signal monitoring device. Output processor 50 may also generate control data in response to alert message for controlling patient treatment device 150 and automatically change operational settings and/or treatment provided to a patient. Treatment device 150 includes, for example, an infusion pump for controlling delivery of at least one medication to a patient or a ventilator. It should be noted that treatment device 150 may include any device that is coupled to a patient and used to provide healthcare related services to the patient.

Workstation 20 may be connected to destination systems, for example healthcare information system 18 and/or portable electronic devices 19, and patient care devices 100 via network 16. Network 16 is preferably adapted to use one or more data formats, otherwise called protocols, depending on the type and/or configuration of the various elements in system 10. Examples of the information system data formats include, without limitation, an RS232 protocol, an Ethernet protocol, a Medical Interface Bus (MIB) compatible protocol, DICOM protocol, an Internet Protocol (IP) data format, a local area network (LAN) protocol, a wide area network (WAN) protocol, an IEEE bus compatible protocol, and a Health Level Seven (HL7) protocol, HTTP and HTTPS. Network communication paths may be formed as a wired or wireless (W/WL) connection. The wireless connection permits a person using system 10 to be mobile beyond the distance permitted with a wired connection. Alternatively, workstation may be directly connected to any of destination systems and/or care devices using either wired or wireless communication protocols.

An alternative embodiment of system 10, with reference to FIG. 1, processes data representative of heart electrical signals to identify a cardiac condition. The system 10 may also include an acquisition processor for acquiring data representing a sequence of successive pulses of a type of electrical heart waveform of a patient and a computation processor for calculating a pulse interval irregularity measure based on a sum of time interval differences occurring between pairs of successive pulses of the sequence of successive pulses and a mean time interval of successive pulses of the sequence and excluding time interval differences exceeding a predetermined maximum threshold from the sum and for comparing a calculated pulse interval irregularity measure with a predetermined irregularity measure threshold. An output processor generates data representing an alert message in response to the calculated pulse interval irregularity measure exceeding the predetermined threshold. Within the system an individual time interval difference may include a difference between a time interval occurring between a successive pair of pulses of the sequence and a mean time interval determined for successive pairs of pulses occurring in the sequence. The computation processor may calculate the irregularity measure δ as:

$$\delta = \sum_{i=2}^{M} \frac{|RR_i - RR_{i-1}|}{(M-1)*\overline{RR}}$$

where RR represent the interval between two consecutive R waves, $\overline{RR}$ is the mean value of the selected RR intervals and |a| represents the absolute value of a. In further alternative embodiments computation processor may calculate mean value of intervals all eligible intervals could be used in a calculation.

Figure 2:
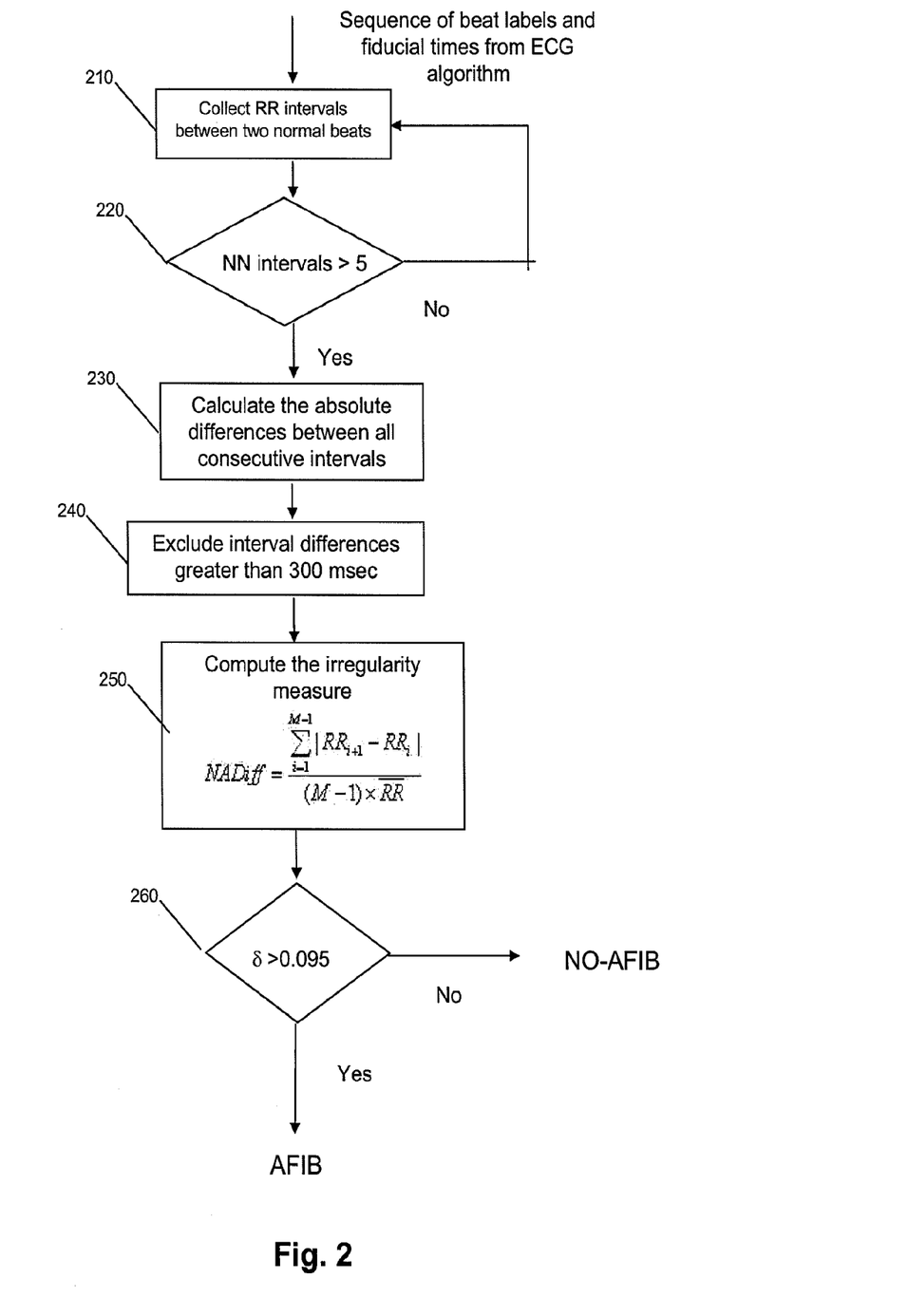
FIG. 2 is a flow diagram of an algorithm for determining cardiac signal irregularity implemented by the cardiac condition detection system according to invention principles.

The input to the AFIB algorithm is the sequence of the beat labels and R-wave fiducials that are processed by the ECG algorithm. The algorithm stores 30 heart beats, for example including different kinds of classifications (i.e. beat labels: Normal, Ventricular, Unknown . . . ) and measures the RR irregularity in that frame. The intervals between two normal beats are used and the system excludes other intervals. If the number of Normal-Normal intervals is greater than 5 in a 30 beat frame, the algorithm calculates the irregularity measure NADiff which is defined as:

$$\delta = \frac{\sum_{i=1}^{M-1} |RR_{i+1} - RR_i|}{(M-1) \times \overline{RR}}$$

where RR represent the interval between two consecutive R waves, $\overline{RR}$ is the mean value of the selected RR intervals and $|RR_i-RR_{i-1}|$ represents the absolute value thereof. To improve the performance of the algorithm against false positives due to the APB's the interval differences ($|RR_{i+i}-RR_i|$) that are greater than 300 msec, for example are excluded. The processing of the data of the AFIB databases shows that such interval irregularities are mostly due to non-AFIB rhythms. To detect AFIB the system examines the value of NADiff for each frame of ECG signal. If NADiff is larger than 0.095 the algorithm sets the AFIB flag on otherwise it reports NO-AFIB. This operation is depicted in the flow diagram in FIG. 2.

FIG. 2 is a flow diagram of an algorithm for controlling operation of system 10 and which is discussed with reference to the hardware for implementing the algorithm shown in FIG. 1. At 210, the acquisition processor 30 employs an ECG monitoring algorithm to acquire a sequence of electrical signals representing patient heart beats and fiducial times of the heart beat and the computation processor 40 calculates data representing RR intervals between two normal heart beats. At step 220, computation processor 40 queries whether the number of RR intervals calculated by computation processor 40 is greater than 5. If, not, computation processor 40 calculates additional RR intervals until at least 5 RR intervals are calculated. When the result of the query of step 220 is greater than 5, computation processor 40 calculates, in step 230, the absolute difference between all consecutive RR intervals. The result of the calculation in step 230 having RR intervals greater than 300 milliseconds in length are excluded from further evaluation in step 240. Calculation processor 40 computes the irregularity measure of the RR intervals δ in step 250 as, $$\delta = \frac{\sum_{i=1}^{M-1} |RR_{i+1} - RR_i|}{(M-1) \times \overline{RR}}$$

Computation processor 40, in step 260, further queries the result of the calculation in step 250 to determine if δ is greater than 0.095. If the result of the query in step 260 is greater than 0.095 than computation processor 40 controls output processor to generate an alert message indicating that the patient being monitored is in AFIB. If the result of query 260 is less than 0.095, then it is determined that the patient is not in AFIB. In response to a determination that the patient is not in AFIB, output processor 50 automatically generates a message including a patient status identifying the time at which the irregularity measurement was performed and the result thereof. This message may be communicated to a destination system, for example, for incorporation into an active patient record associated with the particular patient.

Alternatively, the steps listed in FIG. 2 may be implemented as executable code that is stored on a computer readable medium, for example, an optical disk or hard disk drive. The steps shown in FIG. 2 may be implemented as a single segment of code encompassing all steps shown in FIG. 2 or, as multiple segments of computer code wherein respective segments include subsets of instructions corresponding to the steps of FIG. 2. The steps are encoded in any programming language able to be stored on a computer readable medium to be read and implemented by a computer, for example Java, XML, etc. Moreover, the algorithms described above with respect to FIG. 1 controlling the operation of the specific purpose processors may also be encoded on a computer readable medium as individual or combined segments of computer readable code to be implemented by a computer system.

Figure 3:
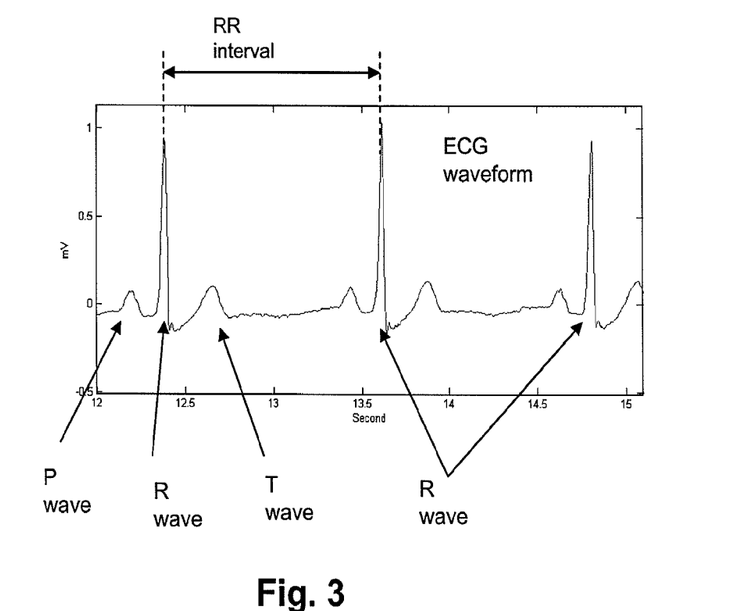
FIGS. 3-5 are exemplary waveform diagrams showing cardiac waveform data for use by the cardiac condition detection system according to invention principles.

FIG. 3 illustrates an exemplary ECG trace including successive heartbeats. A typical ECG tracing of a normal heartbeat (or cardiac cycle) consists of a P wave, a QRS interval and a T-wave. A small U wave is normally visible in 50 to 75% of ECGs. The baseline voltage of the electrocardiogram is known as the isoelectric line, measured as the portion of the ECG tracing following the T-wave and preceding the next P wave. During normal atrial depolarization, the main electrical vector spreads from the right atrium to the left atrium. This is identified as the P wave on the ECG. The QRS interval corresponds to the depolarization of the ventricles. Because the ventricles contain more muscle mass than the atria, the QRS interval is larger than the P wave. In addition, the QRS interval tends to look "spiked" rather than rounded due to the increase in conduction velocity. The T-wave represents the repolarization (or recovery) of the ventricles. The interval from the beginning of the QRS interval to the apex of the T-wave is referred to as the absolute refractory period. The last half of the T-wave is referred to as the relative refractory period (or vulnerable period). In analyzing successive heartbeats, as performed by system 10, the RR-interval is the time between successive R-peaks. Data representing the RR interval is acquired for further processing to determine if the patient is in AFIB.

Figure 4:
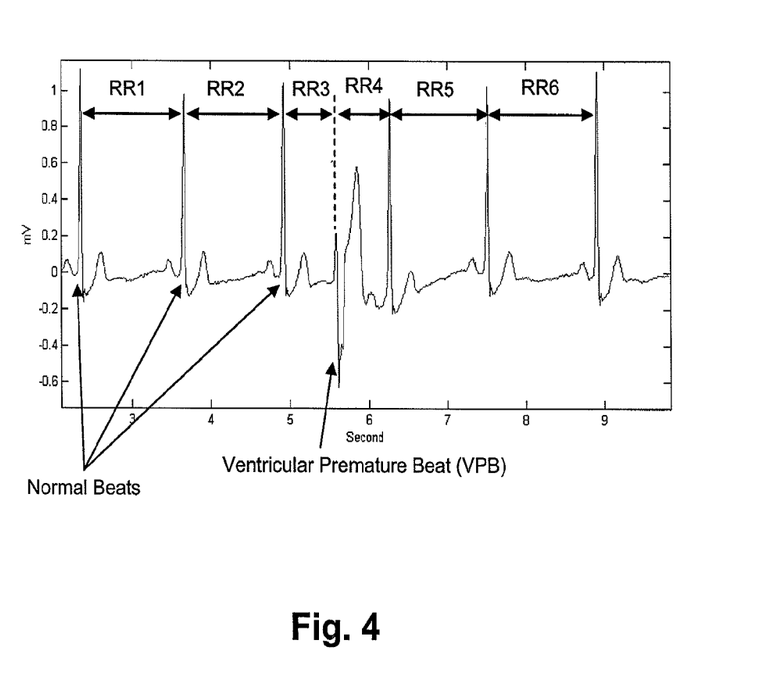

FIG. 4 is an exemplary waveform of successive heartbeats including the plurality of RR-intervals measured and acquired by system 10. The waveform shown herein is a graphical representation of input data associated with a patient which acquired by system 10 for use in calculating an irregularity measure and accurately determining if the data is indicative of AFIB. The waveform of FIG. 4 includes a plurality of successive normal heartbeats which are labeled as such. Also shown is an abnormal heartbeat indicated by the arrow labeled Ventricular Premature Beat (VPB). System 10 automatically recognizes and excludes from further analysis RR interval data associated with abnormal waveform patterns, for example VPBs. Because the VPB indicates an abnormality that is known to be unrelated to AFIB detection, the RR interval data that borders the abnormal beat on each side (RR3 and RR4) is excluded from the irregularity calculation performed by computation processor 40 (FIG. 1). It should be noted that VPB being automatically excluded by system 10 in the irregularity calculation is merely exemplary. System 10 is able to automatically exclude any type of ventricular (or other) abnormality to ensure that any calculated irregularity measure is accurate. The different types of abnormalities able to be automatically excluded may be derived from a local repository located within workstation 20 (FIG. 1) or remotely from workstation 20 and connected via network 16. Moreover, upon detection of an abnormality by system 10, output processor 50 may generate an exclusion message including information identifying a type of detected and excluded abnormality as well as at least one of (a) patient identification information, (b) time of detection, (c) location of the patient and (d) reason for exclusion. The exclusion message data may be communicated to a destination system for incorporation into a patient health record, for example, or be provided to a healthcare professional for further evaluation.

Figure 5:
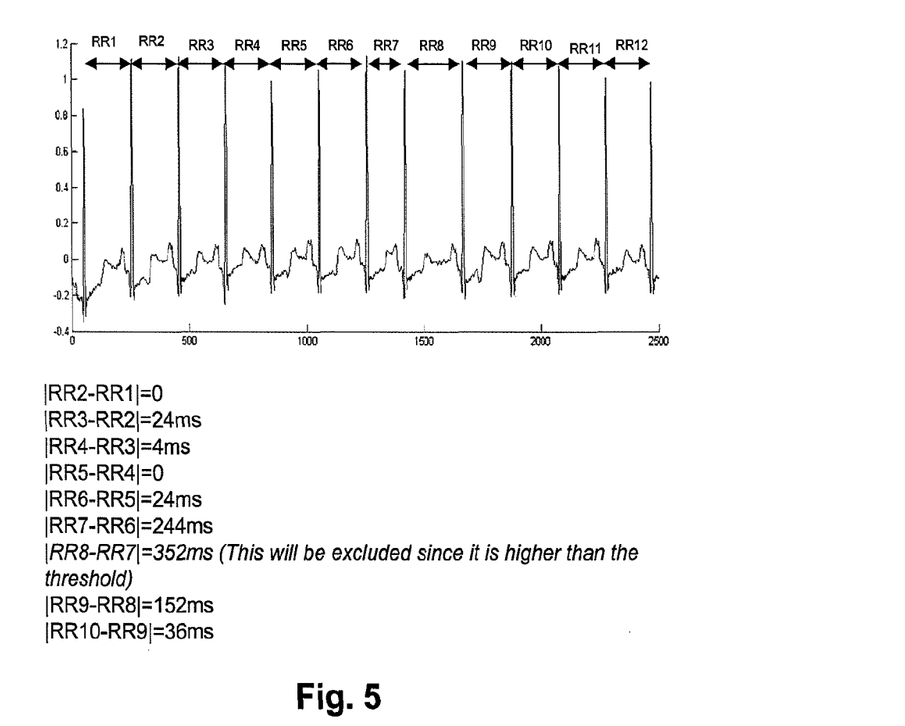

FIG. 5 is an exemplary waveform of a series of successive heartbeats acquired from an ECG monitor 15 (FIG. 1) by acquisition processor 30. This waveform represents input data for use by calculation processor 40 in calculating an irregularity measure that is indicative of AFIB in the patient. The waveform is labeled to show the RR interval of the successively acquired beats. Prior to calculating the irregularity measure, computation processor 40 implements the algorithm described above to calculate the absolute difference between successive RR intervals. The calculations for the successive RR intervals are shown there. The result of this calculation is compared to a threshold maximum value, for example 290 milliseconds, to determine if the calculated RR interval value is to be used in calculating the irregularity measure which may be indicative of patient AFIB. As shown herein, the RR8-RR7 value is listed as 352 milliseconds which is greater than the maximum threshold value of 290 milliseconds. Therefore, this value will be excluded from any further calculation preformed by system 10 because it will likely skew the resulting irregularity measure thus reducing the accuracy of detecting (or predicting) AFIB in the patient.

Figure 6:
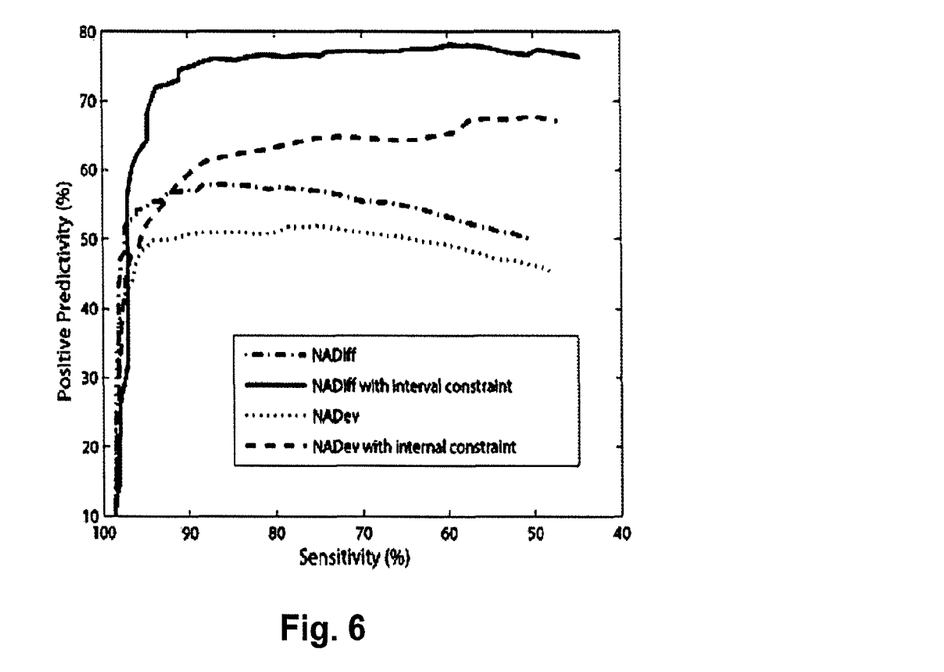
FIGS. 6-8 are graphical depictions of the sensitivity and predictivity of identifying AFIB using the cardiac condition detection system according to invention principles.
Figure 7:
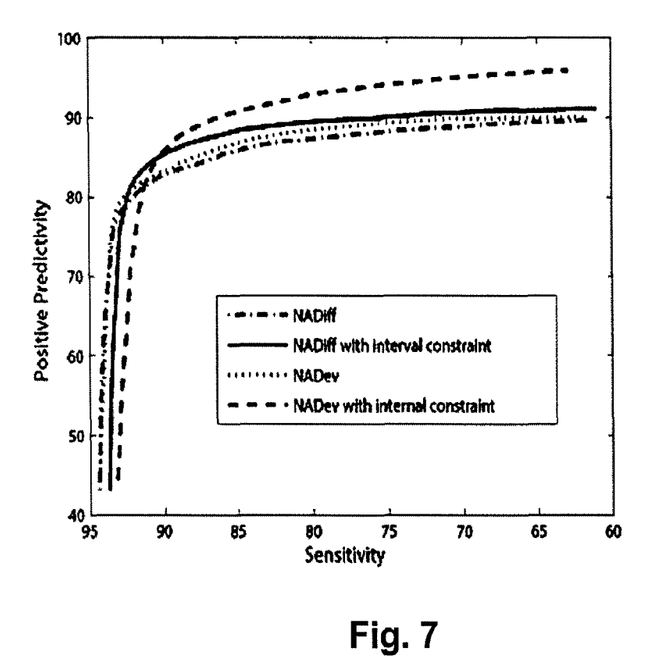
Figure 8:
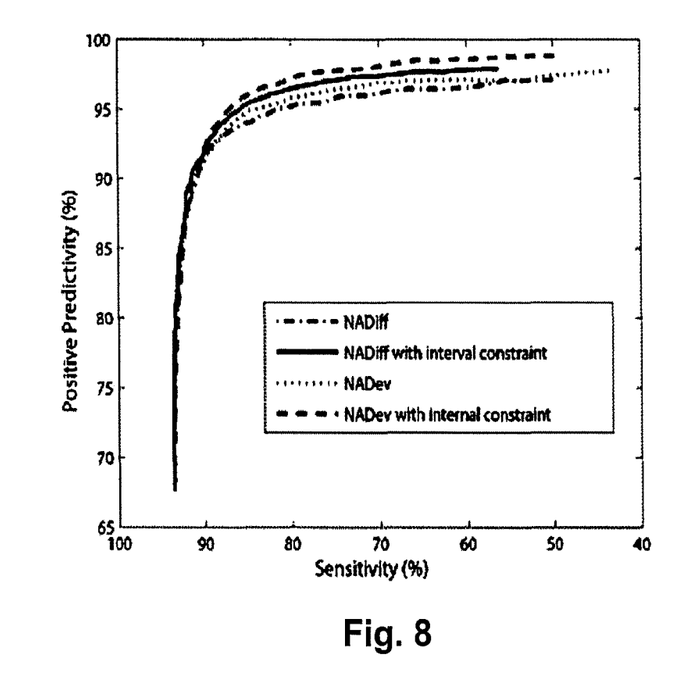

FIGS. 6-8 are graphical representations of Receiver Operating Curves (ROC) which illustrate the effectiveness of the irregularity calculation algorithm implemented by system 10 in sensing and predicting AFIB in a patient. The system provides different RR irregularity measures suitable for cardiac condition (e.g., Atrial Fibrillation (AFIB)) detection in ECG monitors, for example. A first measure is an absolute deviation and a second measure is based on the difference between successive RR intervals. A sequence of RR intervals is processed by computation processor 30 (FIG. 1). Computation processor 30 applies constraints on length and beat classifications to provide criteria for detection of AFIB. In an illustration of operation, the ROC's of FIGS. 6-8 are used to analyze and compare the performance of the different measures against different test databases that include data corresponding to different cardiac arrhythmias.

The three databases to evaluate the performance of the two irregularity calculation algorithms implemented by system 10 were:
1. MIT-BIH Arrhythmia Database: This is a known database obtained from 47 subjects which includes 48 half-hour excerpts of two-channel ambulatory ECG recordings. This database contains 23 records chosen randomly and 25 records to include a variety of rare but clinically significant phenomena. Therefore it is a useful database to examine the measures in terms of false detections. The system excludes four records (102, 104, 107 and 217) of this database containing paced beats for this experiment.

The MIT-BIH Arrhythmia Database includes 115 AFIB episodes (almost 2.2 hours) where 44 episodes are less than 10 seconds and 87 episodes are less than 1 minute. Therefore the AFIB episodes mostly represent paroxysmal AFIB.

2. MIT-BIH AFIB Database: This database contains 25 ten-hour records (23 available through Physionet.org) obtained from Holter tapes of 25 subjects. It includes about 300 episodes of AFIB (almost 93 hours) where 105 episodes are less than 1 minute and 242 episodes are less than 10 minutes. This database is useful to examine the sensitivity of methods since it has a variety of AFIB cases however they mostly represent paroxysmal AFIB.

3. Proprietary Medical AFIB Database: This database was obtained from 71 subjects most of them experiencing chronic AFIB. It contains 71 records of multi-lead ECG recordings. Patients usually went through cardioversion and their rhythm changed to normal most of the time after cardioversion. The database was annotated by one cardiologist for determination of the beginning and end of AFIB episodes. The system processed 28 records (30 hours) that include 18 episodes (almost 15 hour) of AFIB and represent variety of chronic AFIB cases.

The beat annotation for MIT-BIH AFIB and Proprietary AFIB databases was generated by an ECG Monitoring Algorithm that classifies the beats as Normal or Ventricular. A reference beat annotation for MIT-BIH Arrhythmia database was provided by Physionet.

Records of the three databases were divided into frames each containing 30 heart beats. For each frame the intervals associated to VPB's are excluded and the system calculated the NADev and NADiff. The interval constraints previously explained are applied and the system calculates the NADev and NADiff again. The parameters of NADev interval constraints were set as $\alpha=0.75$ and $\beta=1.4$. The interval difference threshold $\gamma$ for NADiff was set to 300 ms. These parameters were initially set experimentally in order to obtain optimum performance.

Two measures are compared in terms of Sensitivity (SE), i.e. the probability of detection, and Positive Predictivity (PP), i.e. the probability of correct detection. They were obtained as SE=TP/(TP+FN) and PP=TP/(TP+FP) where TP is the duration of True Positives (AFIB is classified as AFIB), FN is the duration of False Negatives (AFIB is classified as non-AFIB) and FP is the duration of False Positives (non-AFIB is classified as AFIB).

To obtain SE and PP threshold values are determined for AFIB detection based on NADev and NADiff which are termed $THR_{Dev}$ and $THR_{Diff}$ respectively. The SE and PP are calculated for a range of values of $THR_{Dev}$ and $THR_{Diff}$ and ROC curves are plotted for the individual measures with and without interval constraints. The threshold values that result in a reasonable trade off between SE and PP for AFIB detection are selected.

FIG. 6 represents the ROC's corresponding to NADev and NADiff irregularity measures applied to the MIT-BIH Arrhythmia Database with and without the interval constraints. As it was pointed out before MIT-BIH Arrhythmia Database is helpful for evaluating PP of AFIB detection methods because it contains a variety of rare events other than AFIB that may involve RR interval irregularity. It is apparent in FIG. 6 that AFIB detection based on NADiff results in a better PP than the one based on NADev before and after applying the interval constraint. Also the interval constraint improves the PP of both methods however AFIB detection based on NADiff clearly has superior performance.

FIG. 7 represents the ROC's corresponding to NADev and NADiff irregularity measures applied to the MIT-BIH AFIB Database with and without the interval constraints. This database has a variety of paroxysmal AFIB cases which is helpful to evaluate the sensitivity of AFIB detection methods. However the PP over this database may not represent the real practice statistics because it does not contain a variety of other events. FIG. 7 shows the performance of the two methods are very close before applying the interval constraints. Even after applying the interval constraints, ROC's of both methods are close but the method based on NADev loses more SE while gaining more PP compared to the method based on NADiff.

FIG. 8 represents the ROC's corresponding to NADev and NADiff irregularity measures applied to the Proprietary Medical AFIB Database with and without the interval constraints. The results show that the performance of both methods are close and applying the interval constraint does not show a significant change in their performance.

The results of the evaluation of system operation are summarized in Table I which shows the performance of AFIB detection methods based on NADev and NADiff with interval constraints for the three different databases used in this study. The values of $THR_{Dev}$ and $THR_{Diff}$ were set to 0.074 and 0.095 respectively to result in a reasonable trade off between SE and PP on all databases.

TABLE 1

Performance of AFIB detection methods

|  | NADev with interval constraint | | NADiff with interval constraint | |
| --- | --- | --- | --- | --- |
|  | SE | PP | SE | PP |
| MIT-BIH Arrhythmia DB | 91% | 58% | 92% | 73% |
| MIT-BIH AFIB DB | 86% | 90% | 89% | 87% |
| Proprietary Medical AFIB DB | 85% | 96% | 87% | 94% |

The system advantageously reduces the number of false positives and provides higher sensitivity in detection of short episodes of AFIB. The AFIB detection is advantageously combined with a defibrillator or ECG unit. The system also advantageously determines subsets of eligible intervals and interval differences, and the inclusion of eligible intervals and interval differences in calculating the irregularity measure excluding other intervals. The system is implemented by an ECG patient monitor to provide alarm notification, or other type of alert notification, of an AFIB event to the clinician. Further, in response to detection of AFIB, an alarm message may be sent to a physician or clinician, treatment may automatically be administered, terminated or changed (e.g. via change of medical device settings) such as defibrillation or application of heart pacing signals and documentation of the detection may be automatically prepared.

The two RR irregularity measures employed by the system are computationally efficient which is desirable for AFIB detection algorithm in ECG monitoring devices. The constraints on the RR intervals used in RR irregularity measure generation advantageously improve heart condition detection of both measures. The results (especially for MIT-BIH Arrhythmia Database) showed that AFIB detection based on NADiff results in a better performance than the one based on NADev. The illustrated operation results are based on applying the AFIB detection system on frames of ECG signal containing 30 heart beats. The performance is further improved by applying a low pass filter on AFIB detection results. This improves the performance for data in the MIT-BIH Arrhythmia database which contains isolated episodes of false AFIB detection. The system excludes VPB's and added constraints on RR interval data provided to the irregularity measure generator to decrease the number of false detections. The system may also advantageously use P wave characteristics in addition to RR irregularity measures to further improve the performance of AFIB detection.

Although the invention has been described in terms of exemplary embodiments, it is not limited thereto. Rather, the appended claims should be construed broadly to include other variants and embodiments of the invention which may be made by those skilled in the art without departing from the scope and range of equivalents of the invention. This disclosure is intended to cover any adaptations or variations of the embodiments discussed herein.

What is claimed is:

1. A cardiac condition data processing system for processing data representative of heart electrical signals to identify a cardiac condition, comprising:
    an acquisition processor configured to acquire data representing a sequence of successive pulses of a type of electrical heart waveform of a patient;
    a computation processor configured to,
        calculate a pulse interval irregularity measure based on a sum of time interval differences occurring between pairs of successive pulses of said sequence of successive pulses, the time interval differences exceeding a predetermined maximum threshold are excluded from said sum prior to use in calculating the pulse interval irregularity measure and
        compare a calculated pulse interval irregularity measure with a predetermined irregularity measure threshold; and
    an output processor configured to generate data representing an alert message in response to said calculated pulse interval irregularity measure exceeding said predetermined threshold.
2. The system according to claim 1, wherein each of the time interval differences comprises a difference between a first time interval occurring between a first pair of pulses and a second time interval occurring between a subsequent second pair of pulses, said first and second pair of pulses sharing a common pulse.
3. The system according to claim 1, including a defibrillator, for one of enabling a user to initiate defibrillation in response to said alert message and automatically initiating defibrillation in response to said alert message.
4. The system according to claim 1, including a heart pacing signal generator for automatically initiating generation of a heart pacing signal in response to said alert message.
5. The system according to claim 1, including a patient parameter monitoring device for automatically changing monitoring device operational settings in response to said alert message.
6. The system according to claim 1, including a treatment device for automatically changing operational settings and treatment provided to a patient in response to said alert message.
7. The system according to claim 1, wherein said predetermined maximum threshold from said sum comprises at least 290 milliseconds.
8. The system according to claim 1, wherein said sequence of successive pulses of said type of electrical heart waveform of a patient comprises R-wave pulses.
9. The system according to claim 8, wherein each pulse of successive pulses corresponds to a normal heart beat.
10. The system according to claim 9, wherein said computation processor inhibits calculation if the number of pairs of consecutive normal heart beats in a first predetermined number of successive heart beats is less than a second predetermined number.
11. The system according to claim 1, wherein said computation processor calculates said pulse interval irregularity measure based on a sum of the absolute value of said time interval differences.
12. The system according to claim 11, wherein said computation processor calculates said pulse interval irregularity measure by dividing said sum of the absolute value of said time interval differences by a mean of the pulse intervals.
13. The system according to claim 12, wherein said computation processor calculates said pulse interval irregularity measure by dividing said sum of the absolute value of said time interval differences by said mean of the pulse intervals multiplied by the number of intervals involved.
14. The system according to claim 13, wherein said computation processor calculates said irregularity measure $\delta$ as:

$$\delta = \sum_{i=2}^{M} \frac{|RR_i - RR_{i-1}|}{(M-1)*\overline{RR}}$$

where M represents the number of intervals, RR represent the interval between two consecutive R waves, $\overline{RR}$ is the mean value of the selected RR intervals and |a| represents the absolute value of a.

15. The system according to claim 1, wherein said predetermined maximum threshold is adaptively varied in response to at least one of, (a) mean pulse time interval size, (b) number of said pairs of consecutive normal heart beats between said sequence of successive pulses and (c) a previously calculated irregularity measure value.
16. The system according to claim 1, wherein said predetermined irregularity measure threshold is adaptively varied in response to at least one of, (a) mean pulse time interval size, (b) number of said pairs of consecutive normal heart beats between said sequence of successive pulses and (c) a previously calculated irregularity measure value.
17. A cardiac condition data processing system for processing data representative of heart electrical signals to identify a cardiac condition, comprising:
    an acquisition processor configured to acquire data representing a sequence of successive pulses of a type of electrical heart waveform of a patient;
    a computation processor configured to,
        calculate a pulse interval irregularity measure based on a sum of time interval differences occurring between pairs of successive pulses of said sequence of successive pulses and a mean time interval of successive pulses of said sequence, the time interval differences exceeding a predetermined maximum threshold are excluded from said sum prior to use in calculating the pulse interval irregularity measure;
        compare a calculated pulse interval irregularity measure with a predetermined irregularity measure threshold; and
    an output processor configured to generate data representing an alert message in response to said calculated pulse interval irregularity measure exceeding said predetermined threshold.

18. The system according to claim 17, wherein
each of the time interval differences comprises a difference between a time interval occurring between a successive pair of pulses of said sequence and a mean time interval determined for successive pairs of pulses occurring in said sequence.

19. The system according to claim 18, wherein
said computation processor calculates said pulse interval irregularity measure δ as:

$$\delta = \sum_{i=2}^{M} \frac{|RR_i - RR_{i-1}|}{(M-1) * \overline{RR}}$$

where M represents the number of intervals, RR represent the interval between two consecutive R waves, $\overline{RR}$ is the mean value of the selected RR intervals and |a| represents the absolute value of a.

20. A method of processing data representative of heart electrical signals to identify a cardiac condition, comprising the activities of:

acquiring data representing a sequence of successive pulses of a type of electrical heart waveform of a patient;

calculating a pulse interval irregularity measure based on a sum of time interval differences occurring between pairs of successive pulses of said sequence of successive pulse, the time interval differences exceeding a predetermined maximum threshold are excluded from said sum prior to use in calculating the pulse interval irregularity measure; and comparing a calculated pulse interval irregularity measure with a predetermined irregularity measure threshold; and generating data representing an alert message in response to said calculated pulse interval irregularity measure exceeding said predetermined threshold.

\* \* \* \* \*